United States Patent [19]

Barham et al.

[11] 4,427,614

[45] Jan. 24, 1984

[54] 3-HYDROXYBUTYRIC ACID POLYMERS

[75] Inventors: Peter J. Barham, Bristol; Paul A. Holmes, Middlesbrough, both of England

[73] Assignee: Imperial Chemical Industries PLC, London, England

[21] Appl. No.: 434,229

[22] Filed: Oct. 14, 1982

[30] Foreign Application Priority Data

Oct. 29, 1981 [GB] United Kingdom ............... 8132681
Mar. 24, 1982 [GB] United Kingdom ............... 8208577

[51] Int. Cl.$^3$ .............................................. D01D 5/12
[52] U.S. Cl. .............................. 264/210.1; 264/290.2; 264/299; 528/361

[58] Field of Search ............... 264/210.1, 290.2, 299; 528/361

[56] References Cited

U.S. PATENT DOCUMENTS

4,360,488  4/1982  Barham et al. ............... 264/210.1

*Primary Examiner*—Jay H. Woo
*Attorney, Agent, or Firm*—Cushman, Darby & Cushman

[57] ABSTRACT

A solvent-free preform of a 3-hydroxybutyric acid polymer is subjected to a compression step to reduce its thickness by at least 5% and the compressed preform is then drawn uni- or bi- axially to induce orientation.

12 Claims, No Drawings

3-HYDROXYBUTYRIC ACID POLYMERS

This invention relates to 3-hydroxybutyric acid polymers.

Poly(3-hydroxybutyric acid) is a thermoplastic polyester consisting of repeat units of the formula

—CH(CH$_3$).CH$_2$.CO.O— which is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material.

The polymer is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote accumulation of the polymer, at least part of the cultivation is preferably conducted under conditions wherein there is a limitation of a nutrient that is essential for growth of the micro-organism but which is not required for polymer accumulation. Examples of suitable processes are described in European Patent Specifications 15669 and 46344.

Polymers containing both 3-hydroxybutyric acid units and other hydroxy-carboxylic acid units, such as 3-hydroxyvaleric acid units, can also be produced microbiologically. Thus a microbiologically produced heteropolymer containing 3-hydroxybutyric acid and 3-hydroxyvaleric acid residues is described by Wallen et al in "Environmental Science and Technology" 8 (1974) 576–9. Also, as described in European Patent Specification 52459 various copolymers can be produced by cultivating the micro-organism on certain substrates, such as propionic acid which gives rise to 3-hydroxyvaleric acid units in the copolymer.

While cells containing the polymer can be used as such as a moulding material, for example as described in U.S. Pat. No. 3,107,172, it is generally desirable to separate the polymer from the remainder of the cell material.

Methods that have been proposed to effect this separation include breakage of the cells by methods such as treatment with acetone, followed by extraction of the polymer from the broken cells by treatment with a solvent in which the polymer is soluble. Examples of such processes are described in U.S. Pat. Nos. 3,036,959 and 3,044,942 in which the solvents employed are pyridine or mixture of methylene chloride and ethanol. Other extraction solvents for the polymer in the form in which it is produced in the cells include cyclic carbonates such as 1,2-propylene carbonate (see U.S. Pat. No. 4,101,533); chloroform (U.S. Pat. No. 3,275,610); and 1,2-dichloroethane (as disclosed in European Patent Specification 15123).

U.S. Pat. No. 3,275,610 discloses other methods of cell breakage viz. ultrasonic vibration, grinding, French pressing, freezing/thawing cycles and lysozyme treatment, while, as described in the aforementioned European Patent Specification 15123, spray or flash drying of the suspension of cells as produced by culturing the micro-organism can also cause sufficient cell breakage to enable the polymer to be extracted from the cells.

Copolymers can also be made containing units of other hydroxycarboxylic acids and/or units derived from diols, e.g. ethylene glycol, and/or dicarboxylic acids, e.g. isophthalic acid, by ester interchange occurring when the microbiologically produced polymer or copolymer is melted with such a hydroxycarboxylic acid, lactone thereof, e.g. pivalolactone, diol, dicarboxylic acid and/or polyester produced therefrom.

In the following description therefore, by the term HB polymer we mean not only 3-hydroxybutyric acid homopolymer, but also copolymers as described above, provided that the 3-hydroxybutyric acid residues form at least 40 mole %, and preferably at least 50 mole % and most preferably at least 80 mole % of the polymer chain.

In the production of some shaped articles, such as fibres, ribbons, films, and bottles, it is often desired to induce a degree of orientation into the product.

Conventional orientation techniques involve
(a) forming an amorphous preform and then subjecting the preform to tensile stress, e.g. uni- or bi-axially, usually at a temperature above, but near to, the glass transition temperature, Tg, to cause the preform to yield and draw.
(b) drawing a crystalline preform at a temperature below, but near to, the crystalline melting point, Tm.

Technique (a) is often adopted for polyesters, e.g. polyethylene terephthalate, and polyamides e.g. poly hexa methylene adipamide (Nylon 66) and poly caprolactam (Nylon 6), whereas technique (b) is often adopted for olefin polymers, e.g. polypropylene and polyethylene.

We have found that orientation of HB polymers by these techniques is difficult: the conditions for the production of a suitable preform and for drawing are critical and difficult to reproduce consistently. In general the preforms are brittle, even at elevated temperatures, and tend to break before they yield and orient.

One particular orientation technique for HB polymers is disclosed in European Patent Specification 24810. In the process described therein orientation was induced by rolling or drawing "parchments" made by squeezing solvent from a gel formed from a solution of a HB homopolymer in a poor solvent therefor. The temperature required depended on the residual solvent content of the "parchment"; relatively high temperatures, of the order of the melting point of the "parchment", were required when the latter had been dried to remove residual solvent. These parchments were a special form of the polymer exhibiting a lower melting point (circa 150° C.) than usual and showing no signs of the granular spherulitic crystallisation exhibited by articles formed from polymers by melt processing.

We have now found that if solvent free preforms e.g. made by melt fabrication or solution casting, of HB polymers are subjected to compressive forces, e.g. by rolling, at temperatures below the crystalline melting point, the preform is rendered more ductile thus enabling further, conventional, orientation processes to be applied.

Accordingly we provide a process for the production of a shaped article from a HB polymer comprising subjecting a solvent-free preform of the polymer to compressive force at a temperature between the glass transition temperature (Tg) and the crystalline melting point (Tm) of the polymer so that its thickness is reduced by at least 5%, and thereafter drawing the compressed preform uni- or bi-axially.

The compressive force may be applied in a number of ways. Thus a sheet or plaque of the polymer may simply be subjected to pressure between the plattens of a press maintained at the desired temperature.

Another technique is to subject a preform to a rolling operation e.g. by passing the preform through the nip of a pair of nip rollers maintained at the desired temperature. The nip may be suitably profiled so as to produce a rolled product of the desired cross-sectional configuration.

An alternative technique involves extrusion of the preform in the solid state through a die maintained at the desired temperature. Such a technique is described in "Ultra High Modulus Polymers", edited by A. Ciferri and I. M. Ward, Applied Science Publishers, London 1979. The preform may be pushed through the die which is usually tapered, by means of e.g. hydrostatic pressure. In addition, and particularly after commencement of such 'cold' extrusion, the extrusion may be assisted by pulling the extrudate emerging from the die. The passage of the preform through the die applies the desired compressive force.

Initially the preform has a thickness $t_o$, a width, $b_o$, and a length $l_o$. After a compression operation it has thickness $t_1$, width $b_1$, and length $l_1$.

The preform may be subjected to a plurality of compression operations, each one progressively reducing the thickness of the preform: thus it may be passed through a series of two or more pairs of nip rollers. Preferably each compression operation reduces the thickness of the preform by at least 5%, i.e.

$$t_n/t_{n-1} \leq 0.95$$

where $t_n$ is the thickness after the $n^{th}$ compression operation and $t_{n-1}$ is the thickness before the $n^{th}$ compression step.

Where the compression is affected in stages by rolling by passing the preform between pairs of nip rollers, in some cases it may be desirable to roll the preform in a first direction and then to subject the rolled preform to a further rolling step in a direction at right angles to the first direction.

The total thickness reduction is preferably at least 20%, i.e. $t_n/t_o \leq 0.8$ where $t_n$ is the final thickness after all the compression operations.

Where the preform is extruded through a die, the thickness $t_n$ is considered to be the corresponding die dimension: it will be appreciated that the actual thickness of the extrudate may well be less than $t_n$ if a tensile force is applied to the extrudate, e.g. to assist passage of the preform through the die.

The cross-sectional area A is herein deemed to be determined by the width, b, and the thickness, t. The cross-sectional area reduction, $\Delta A$ given by a thickness reduction $\Delta t$ will of course depend on the geometric configuration of the preform and whether the width, b, of the preform alters during the compression operation;

i.e. $\Delta A_1 = A_1 - A_o$ $= f(b_1, t_1) - f(b_o, t_o)$ where the area $A = f(b, t)$.

If a circular disc of diameter $d_o$ (i.e. $b_o = l_o = d_o$) and thickness $t_o$ is pressed between the plattens of a press so that its diameter can increase evenly, then, assuming that any volume change is negligible, since $d_o^2 t_o = d_1^2 t_1$ the proportional thickness reduction, $\Delta A_1/A_o$, is given by $$\frac{\Delta A_1}{A_o} = 1 - \sqrt{1-x}$$

where x is the proportional thickness reduction $\Delta t_1/t_o$.

If a tape, ribbon, or sheet of rectangular cross-section is subjected to compression by rolling through a non-profiled nip, then we have found that generally there is little or no change in width, i.e. $b_1 = b_o$.

Then $\Delta A_1/A_o = \Delta t_1/t_o = x$, i.e. the proportional cross-sectional area reduction equals the proportional thickness reduction. If the increase in length is $\Delta l_1$, the proportional increase in length, i.e. $\Delta l_1/l_o$, otherwise termed the extension, is given by $$\Delta l_1/l_o = x/(1-x)$$

If a preform of circular cross-section, of diameter $d_o$ (i.e. $b_o = t_o = d_o$), is subjected to compression, e.g. by rolling through a profiled nip or by cold extrusion through a die, to give a product of circular cross-section of diameter $d_1$, then the proportional area reduction is given by $$\Delta A_1/A_o = x(2-x)$$

and the extension, assuming any volume change is negligible, is given by $$\frac{\Delta l_1}{l_o} = 1 - \frac{1}{(1-x)^2}$$

Following the compression operation the preform is subjected to a uni- or bi-axial drawing operation, at temperatures between Tg and the melting point of the polymer.

3-hydroxybutyric acid homopolymer has a melting point of about 180° C. and a Tg of about 0° C. HB copolymers, e.g. containing 3-hydroxyvaleric acid units, have lower melting points than the HB homopolymer and often have a lower Tg. The melting point of the HB copolymer will depend on the proportion of comonomer units: for example a copolymer containing about 25 mole % of 3-hydroxyvaleric acid units may have a melting point of the order of 130° C.

The temperature at which the compression operation is conducted is preferably 50° to 150° C. below the melting point of the HB polymer; i.e. for HB homopolymer, the compression operation temperature is preferably in the range 30° to 130° C., particularly 50° to 100° C.

The drawing operation is preferably conducted at 40° to 90° C. below the crystalline melting point of the polymer: i.e. for HB homopolymer in the range 90° to 140° C.

The preform may be produced by, for example, solution casting, but is preferably produced by melt processing. For example it may be billet produced, for example, by compression or injection moulding, or may be a continuous length produced, e.g. by extrusion. In the latter case, the process may be operated in a continuous manner. For example film may be produced by forming a preform by melt extrusion of an HB polymer through a slit die, solidifying and crystallising the preform by passage through a water bath, rolling by passage through at least one pair of nip rolls, followed by uni- or bi-axial drawing, for example by the use of a stenter.

Uniaxially drawn films may in some cases by fibrillated to provide fibres which are of use in the production of sutures.

Fibres can also be made by extrusion of a preform, generally of circular cross-section, followed by the compression operation, e.g. passage through a pair of nip rollers having a profiled surface corresponding to the desired cross-section of the rolled preform. The rolled preform may then be drawn uniaxially. Alternatively the compression operation may be effected by the aforesaid solid state extrusion technique.

In the drawing step the draw ratio in at least one dimension (other than the thickness), i.e. the dimension of the drawn preform: dimension of the compressed preform, is preferably at least 1.5:1, particularly at least 2:1. It has been found that the maximum degree of drawing that can be achieved depends to some extent on the degree of thickness applied during the compression operation. While at least 5% thickness reduction is necessary to permit orientation, too much thickness reduction may limit the maximum overall draw ratio achievable. Preferably the overall draw ratio is at least 3:1 in at least one direction.

Where the preform is drawn uniaxially it is preferred that the compression operation and drawing are conducted so that the overall draw ratio is at least 4:1, particularly at least 5:1.

The invention is illustrated by the following examples. In Examples 1 to 6 the HB polymer was a 3-hydroxybutyric acid homopolymer, hereinafter PHB, produced by aerobic cultivation of *Alcaligenes eutrophus* mutant S 301/C5 (NCIB 11599) on glucose. The PHB was isolated by extraction from the aqueous cell suspension with 1,2-dichloroethane at room temperature followed by separation of the solvent layer, containing the dissolved PHB, from the aqueous layer by decanting. The solution was filtered and then the PHB was precipitated by adding the solution to a methanol/water mixture. The precipitated PHB was separated by filtration, washed with methanol and dried. The dried polymer was formed into a paste with about 10% by weight of chloroform and granulated by passage through a domestic mincer at room temperature. The granules were then dried in an oven to remove the chloroform and melt extruded at 190° C. and regranulated.

EXAMPLE 1

Plaques of the polymer with approximate dimensions 100×30×1.3 mm were prepared by compression moulding the granules at 190° C. for 3 minutes. The plaques were then annealed in a water bath at 60° C. for 10 minutes. The plaques were then rolled at room temperature along their length by passing them through the nip of a pair of unheated rolls of 15 cm width and 7.6 cm diameter rotating at about 10-15 rpm. The plaques were passed through the nip a number of times as set out in Table 1. The thickness and length of the samples were measured before and after rolling to determine the thickness reduction and extension achieved.

Specimens were cut from the samples and the tensile impact strength (according to ASTM D 1922-68) and tensile properties determined at 23° C. The tensile properties were measured on an Instron universal tensile tester using samples of gauge length 20 mm and width 2 mm at a strain rate of 0.5 min$^{-1}$.

In addition to measuring the tensile properties, the tensile testing simulated a further room temperature uniaxial drawing of the rolled samples.

All the rolled samples showed a significant degree of orientation and the improvements in ductility and tensile impact strength is clearly shown in Table 1.

TABLE 1

| Sample | No. of passes through nip | Film thickness (mm) | Percentage thickness reduction | Percentage elongation | Modulus at 0.5% strain (GPa) | Tensile strength (MPa) | Extension to break (%) | Tensile impact strength (kJ·m$^{-2}$) | Overall draw ratio |
|---|---|---|---|---|---|---|---|---|---|
| 1 | 0 | 1.30 | 0 | 0 | 1.00 | 28 | 7.5 | 45 | 1.07:1 |
| 2 | 1 | 1.17 | 10 | 10 | 0.77 | 25 | 23 | 53 | 1.35:1 |
| 3 | 2 | 1.09 | 16 | 18 | 0.64 | 32 | 180 | 77 | 3.3:1 |
| 4 | 3 | 0.88 | 32 | 45 | 0.52 | 30 | 180 | 240 | 4.06:1 |
| 5 | 5 | 0.80 | 38 | 60 | 0.44 | 50 | 200 | 450 | 4.8:1 |
| 6 | 7 | 0.60 | 54 | 110 | 0.48 | 46 | 250 | 550 | 7.35:1 |
| 7 | 10 | 0.40 | 69 | 300 | 0.45 | 45 | 300 | 1000 | 16:1 |

EXAMPLE 2

Plaques were prepared and annealed as described in Example 1 except that the size of the mould was increased to 100×100×1.3 mm. A plaque was repeatedly passed, in the same direction, through the nip of a pair of rollers of 30 cm width and 15 cm diameter heated to 100° C. and rotating at 15 rpm, until its thickness had been reduced by 60% and its extension in the rolling direction was 150%. The extension in the transverse direction was negligible.

Mechanical properties were determined as in Example 1 using specimen cut parallel (MD), and at right angles (TD) to the rolling direction. The results are shown in Table 2.

TABLE 2

|  | Unrolled plaque | Rolled plaque MD | Rolled plaque TD |
|---|---|---|---|
| Modulus at 0.5% strain (GPa) | 1.00 | 0.87 | 1.20 |
| Tensile strength (MPa) | 28 | 58 | 22 |
| Extension to break (%) | 8 | 200 | 8 |
| Tensile impact strength (kJ·m$^{-2}$) | 45 | 700 | 50 |
| Overall draw ratio | 1.08:1 | 7.5:1 | 1.08:1 |

EXAMPLE 3

Example 2 was repeated except that the sample was rotated through 90° after each pass through the nip so that it was sequentially rolled in directions at right angles to one another. Rolling was continued until the total thickness reduction was 58%. The mechanical properties were measured, as described in Example 1, parallel (MD) and at right angles (TD) to the first rolling direction and are shown in Table 3.

The extension in both the MD and TD direction was about 50%.

TABLE 3

|  | Unrolled plaque | Rolled plaque MD | Rolled plaque TD |
|---|---|---|---|
| Modulus at 0.5% strain (GPa) | 1.00 | 0.85 | 0.90 |
| Tensile strength (MPa) | 28 | 40 | 40 |
| Extension to break (%) | 8 | 200 | 220 |
| Tensile impact strength (kJ·m$^{-2}$) | 45 | 180 | 200 |
| Overall draw ratio | 1.08:1 | 4.5:1 | 4.8:1 |

EXAMPLE 4

The melt extruded granules were re-extruded at 190° C. through a 50 mm×1.5 mm slot die to give a ribbon which was passed through a water bath at 60° to crystallise the polymer and then through the nip of the rollers used in Example 1 rotating at about 10 to 15 rpm and heated to about 50° C.

The crystalline ribbon ex-water bath was opaque and brittle. After a single pass through the nip, the ribbon became transparent and ductile. Its length had increased, on passage through the nip, by 120% and its thickness reduced from 1.1 mm to 0.45 mm, i.e. a thickness reduction 59%. Tensile properties of the ribbon were measured, as described in Example 1, in the direction of extrusion (MD) and at right angles thereto (TD) and are shown in Table 4.

TABLE 4

|  | Unrolled ribbon | Rolled ribbon MD | Rolled ribbon TD |
|---|---|---|---|
| Modulus at 0.5% strain (GPa) | 1.5 | 0.90 | 0.94 |
| Tensile strength (MPa) | 35 | 55 | 24* |
| Extension to break (%) | 10 | 70 | 300* |
| Overall draw ratio | 1.1:1 | 3.74:1 | 4:1 |

*The sample yielded and necked at this load and drew to an extension of 300% at constant load until it broke.

EXAMPLE 5

The melt extruded polymer granules were re-extruded at 190° C. through a 4 mm diameter die to give a monofilament that was passed through a water bath at 60° C. to crystallise the polymer. The rate of haul off was adjusted to give considerable draw down of the extrudate and the diameter of the fibre wound up was approximately 1 mm.

The crystalline product was subsequently passed through the profiled nip of a set of jewellers' rolls rotating at 30 to 40 rpm and heated to about 50° C. The nip had a circular profile of diameter slightly less than that of the extruded monofilament.

After rolling the fibres were drawn until they broke at 125° C. in the temperature cabinet of an Instron Universal Testing Machine (model 1122) using extension rates of 1.67 and 16.7 min$^{-1}$. The results are shown in Table 5.

TABLE 5

| Sample Number | % Extension by Rolling | Draw Rate min$^{-1}$ | % Extension by Drawing | Overall Extension Ratio |
|---|---|---|---|---|
| 5.0 | 0 | 1.67 | 10 | 1.10 |
|  |  | 16.7 | 8 | 1.08 |
| 5.1 | 39 | 1.67 | 300 | 5.56 |
|  |  | 16.7 | 93 | 2.68 |
| 5.2 | 58 | 1.67 | 283 | 6.05 |
|  |  | 16.7 | 426 | 8.31 |
| 5.3 | 62 | 1.67 | 290 | 6.32 |
|  |  | 16.7 | 470 | 9.23 |
| 5.4 | 65 | 1.67 | 316 | 6.86 |
|  |  | 16.7 | 390 | 8.09 |
| 5.5 | 81 | 1.67 | 296 | 7.17 |
|  |  | 16.7 | 413 | 9.29 |
| 5.6 | 97 | 1.67 | 223 | 6.36 |
|  |  | 16.7 | 243 | 6.76 |
| 5.7 | 147 | 1.67 | 187 | 7.09 |
|  |  | 16.7 | 210 | 7.66 |
| 5.8 | 220 | 1.67 | 143 | 7.78 |
|  |  | 16.7 | 163 | 8.42 |
| 5.9 | 237 | 1.67 | 170 | 9.10 |
|  |  | 16.7 | 120 | 7.41 |
| 5.10 | 301 | 1.67 | 100 | 8.02 |
|  |  | 16.7 | 93 | 7.74 |

EXAMPLE 6

Four samples of the polymer granules were extruded and then rolled to varying extents using the technique described in Example 5. They were then drawn at 125° C. and a strain rate of 16.7 min$^{-1}$ but the drawing was stopped before the fibres ruptured. After allowing the extended fibres to 'heat set' at 125° C. for five minutes they were removed from the oven and the tensile properties measured at 23° C. with an extension rate of 1 min$^{-1}$. The results are given in Table 6 and indicate that the tensile strength of the monofilament has been increased by a factor of 5 as a result of the cold rolling and hot drawing method.

TABLE 6

| Parameter | Sample Number 6.0 | 6.1 | 6.2 | 6.3 | 6.4 |
|---|---|---|---|---|---|
| % extension by rolling | 0 | 155 | 277 | 144 | 41 |
| % extension by drawing at 16.7 min$^{-1}$, 125° C. | 0 | 185 | 95 | 186 | 375 |
| overall extension ratio | 1.00 | 7.27 | 7.35 | 6.98 | 6.70 |
| final cross sectional area (mm$^2$). | 0.9450 | 0.1207 | 0.0967 | 0.1136 | 0.1654 |
| Young's modulus at 23° C. (GPa) | 2.80 | 1.92 | 2.04 | 1.85 | 1.89 |
| Stress at Break at 23° C. (MPa) | 38 | 220 | 222 | 198 | 191 |
| Extension to Break at 23° C. (%) | 6 | 35 | 34 | 34 | 50 |

EXAMPLE 7

The experiment described in example 5 was repeated using a copolymer of 92% hydroxybutyric acid units and 8% hydroxyvaleric acid units prepared by aerobic cultivation of *Alcaligenes eutrophus* mutant S 301/C5 on a mixed carbon source of glucose and propionic acid. The polymer was extracted and granulated as previously described. The results are given in Table 7.

TABLE 7

| Sample Number | % Extension by Rolling | Draw Rate (min$^{-1}$) | % Extension by Drawing @ 125° C. | Overall Extension Ratio |
|---|---|---|---|---|
| 7.0 | 0 | 1.67 | 20 | 1.20 |
|  |  | 16.7 | 12 | 1.12 |
| 7.1 | 17 | 1.67 | 23 | 1.44 |
|  |  | 16.7 | 20 | 1.40 |
| 7.2 | 46 | 1.67 | 360 | 6.72 |
|  |  | 16.7 | 523 | 9.10 |
| 7.3 | 165 | 1.67 | 126 | 5.99 |

TABLE 7-continued

| Sample Number | % Extension by Rolling | Draw Rate (min$^{-1}$) | % Extension by Drawing @ 125° C. | Overall Extension Ratio |
|---|---|---|---|---|
| | | 16.7 | 155 | 6.76 |
| 7.4 | 72 | 1.67 | 312 | 7.09 |
| | | 16.7 | 444 | 9.36 |

EXAMPLE 8

The copolymer described in Example 7 was used to prepare rolled and drawn fibres for tensile testing at room temperature as described in Example 6. The results are given in Table 8.

TABLE 8

| Parameter | Sample Number | | | |
|---|---|---|---|---|
| | 8.0 | 8.1 | 8.2 | 8.3 |
| % Extension by rolling | 0 | 231 | 215 | 129 |
| % extension by drawing at 16.7 min$^{-1}$, 125° C. | 0 | 95 | 114 | 164 |
| overall extension ratio | 1.0 | 6.45 | 6.74 | 6.05 |
| final cross sectional area (mm$^2$) | 1.200 | 0.1548 | 0.1305 | 0.2576 |
| Young's Modulus at 23° C. (GPa) | 2.20 | 1.69 | 1.36 | 1.27 |
| Stress at Break at 23° C. (MPa) | 34 | 198 | 191 | 131 |
| Extension to Break at 23° C. (%) | 15 | 50 | 60 | 90 |

EXAMPLE 9

Example 5 was repeating using a copolymer of 96% hydroxybutyric acid units and 4% hydroxyvaleric acid units prepared as described in Example 7 but using glucose followed by propionic acid as the carbon source. The results are given in Table 9.

Example 8

| Sample Number | % Extension by Rolling | Draw Rate (min$^{-1}$) | % Extension by Drawing at 125° C. | Overall Extension Ratio |
|---|---|---|---|---|
| 9.0 | 0 | 1.67 | 15 | 1.15 |
| | | 16.7 | 8 | 1.08 |
| 9.1 | 11.6 | 1.67 | 511 | 6.82 |
| | | 16.7 | 810 | 10.16 |
| 9.2 | 51 | 1.67 | 368 | 7.07 |
| | | 16.7 | 402 | 7.58 |
| 9.3 | 142 | 1.67 | 195 | 7.14 |
| | | 16.7 | 224 | 7.84 |
| 9.4 | 173 | 1.67 | 150 | 6.83 |
| | | 16.7 | 159 | 7.07 |

EXAMPLE 10

The experiment described in Example 8 was repeated using the copolymer of Example 9.

TABLE 10

| Parameter | Sample Number | | | |
|---|---|---|---|---|
| | 10.0 | 10.1 | 10.2 | 10.3 |
| % extension by Rolling | 0 | 37 | 148 | 200 |
| % extension by Drawing at 16.7 min$^{-1}$, 125° C. | 0 | 350 | 191 | 137 |
| Overall extension ratio | 1.0 | 6.17 | 7.22 | 7.11 |
| final cross-sectional area (mm$^2$) | 1.200 | 0.2016 | 0.1278 | 0.1449 |
| Young's modulus at 23° C. (GPa) | 2.60 | 1.21 | 1.57 | 1.73 |
| Stress at Break at 23° C. (MPa) | 35 | 147 | 198 | 194 |
| Extension at break at 23° C. (%) | 12 | 30 | 40 | 55 |

EXAMPLE 11

A sample of the polymer used in Example 1 was dissolved in chloroform and the resulting solution filtered through a Whatman GF/B glass fibre filter paper to remove particulate impurities. After concentrating this solution up to approximately 10% w/v polymer on a rotary evaporator it was poured onto a 100×100 mm glass sheet that had been carefully cleaned with toluene to remove grease and placed on a level surface. The volume of solution used was calculated to give a final polymer thickness after solvent evaporation of 1 mm. The solvent was allowed to evaporate slowly and a polythene sheet was suspended over the glass sheet to keep airborne dirt from contaminating the solution.

When dry to the touch, the resulting opaque polymer sheet was edge trimmed and pressed at 23° C. in a press under a force of 20,000 p.s.i. This pressing gave a thickness reduction of about 20%. The film, which was rendered virtually transparent by this pressing process was then biaxially oriented at 150° C. using a T.M. Long stretcher with simultaneous draw rates of 10 min$^{-1}$. The final draw ratios were 4.0:1 in one direction and 4.6:1 in the direction perpendicular thereto and the resulting film was about 25 μm thick.

The mechanical properties of the film were measured using an Instron Universal testing machine with temperature controlled cabinet and a strain rate of 0.4 min$^{-1}$. The results are given in Table 11.

TABLE 11

| Parameter | Temperature °C. | | | | |
|---|---|---|---|---|---|
| | 0 | 25 | 50 | 75 | 100 |
| Modulus @ 1% strain (GPa) | 5.4 | 3.8 | 2.2 | 1.0 | 0.4 |
| Yield stress (MPa) | 81 | 53 | 34 | 25 | 21 |
| Break stress (MPa) | 126 | 102 | 78 | 54 | 30 |
| Extension to break (%) | 60 | 78 | 90 | 105 | 120 |

EXAMPLE 12

Example 11 was repeated with the omission of the cold press stage. It proved impossible to orient this film in the long stretcher under any combination of temperature and draw rate. Sample failure at the grips occurred on every occasion.

EXAMPLE 13

Conventional orientation techniques, i.e. without a cold rolling or solid state compression step, were tried extensively without success with the homo and copolymers used in the previous examples.

It was found that the crystalline polymers were subject to brittle fracture during drawing experiments at all temperatures up to the melting point.

Attempts to draw an amorphous sample of the homopolymer, prepared by injection or compression moulding followed by rapidly quenching the melt to below −5° C., were equally unsuccessful. At temperatures below about −5° C. the samples failed by brittle fracture. Between −2° C. and +7° C. the samples yielded and drew at very low stresses (1-2 MPa) by more than 1000%, but with virtually 100% elastic recovery on release. All attempts to heat set the extended polymer were unsuccessful and resulted in sample failure. Above 7° C. the modulus of the amorphous polymer fell rapidly (0.043 GPa at 10° C.) and tended to fail by necking rupture after about 100 to 200% extension.

Typical results are shown in Table 13.

TABLE 13

| Temp °C. | Strain rate (min$^{-1}$) | Modulus at 0.5% strain (GPa) | Tensile Stress Yield (MPa) | Tensile Stress Break (MPa) | Strain Yield (%) | Strain Break (%) |
|---|---|---|---|---|---|---|
| −20 | 1 | 1.600 | — | 40 | — | 3.5 |
| −10 | 1 | 1.200 | — | 35 | — | 4.5 |
| 0 | 1 | 0.910 | 20 | 10 | 5 | 1140 |
| 0 | 5 | 0.833 | — | 25 | — | 10 |
| +5 | 1 | 0.227 | — | 4.2 | — | 250 |
| +5 | 5 | 0.357 | 8.7 | 3.1 | 5 | 1240 |
| +5 | 10 | 0.360 | — | 6.2 | — | 25 |
| +7 | 10 | 0.250 | 7.75 | 2.3 | 4.5 | 1100 |
| +7 | 25 | — | 11.40 | 1.6 | — | 1500 |
| +10 | 1 | 0.043 | — | 2.2 | — | 100 |
| +15 | 1 | — | — | 0.8 | — | 200 |
| +23 | 1 | — | — | 0.2 | — | 130 |

We claim:

1. A process for the production of a shaped article from a polymeric material in which 3-hydroxybutyric acid residues form at least 40 mole % of the polymer chain comprising subjecting a solvent-free preform of the polymer to compressive force at a temperature between the glass transition temperature and the crystalline melting point of the polymer so that its thickness is reduced by at least 5%, and thereafter drawing the compressed preform uni- or bi-axially.

2. A process according to claim 1 wherein the preform is subjected to said compressive force at a temperature between 50° and 150° C. below the crystalline melting point of the polymer.

3. A process according to claim 1 or claim 2 wherein the compressed preform is drawn at a temperature between 40° to 90° C. below the crystalline melting point of the polymer.

4. A process according to claim 1 wherein the preform is compressed by pressing the preform between the plattens of a press.

5. A process according to claim 1 wherein the preform is compressed by passing the preform through the nip of a pair of nip rollers.

6. A process according to claim 1 wherein the preform is compressed by solid state extrusion of the preform through a die.

7. A process according to claim 5 wherein the preform is passed between the nip of a pair of nip rollers prefiled corresponding to the desired cross-section of the compressed preform and then the rolled preform is drawn uniaxially.

8. A process according to claim 1 wherein the draw ratio, in at least one direction, is at least 1.5:1.

9. A process according to claim 1 wherein the amount of compression and the draw ratio in the drawing step are such that the overall draw ratio in at least one direction is at least 3:1.

10. A process according to claim 9 wherein the compressed preform is drawn uniaxially and the amount of compression and the draw ratio in the drawing step are such that the length of the drawn preform is at least four times the length of the preform prior to the compression step.

11. A process according to claim 1 wherein the preform is produced by melt processing the polymeric material into the desired shape.

12. A process for the production of an oriented film from a polymeric material in which 3-hydroxybutyric acid residues form at least 40 mole % of the polymer chain comprising applying a solution of said polymeric material in a solvent therefore to a surface, evaporating solvent from said solution to form a solution cast film, subjecting said film to a compressive force at a temperature between the glass transition temperature and the crystalline melting point of the polymer so that the thickness of the film is reduced by at least 5%, and thereafter drawing the compressed film uni- or bi-axially.

* * * * *